United States Patent [19]

De Nicola

[11] 4,194,402

[45] Mar. 25, 1980

[54] TESTING MACHINE GRIP

[75] Inventor: Joseph P. De Nicola, Hingham, Mass.

[73] Assignee: Instron Corporation, Canton, Mass.

[21] Appl. No.: 938,697

[22] Filed: Aug. 31, 1978

[51] Int. Cl.$^2$ .............................................. G01N 3/04
[52] U.S. Cl. ................................................... 73/859
[58] Field of Search ......................... 73/859, 856, 857;
269/25, 32, 217; 279/4, 41 R, 41 A

[56] References Cited

U.S. PATENT DOCUMENTS

| | | |
|---|---|---|
| 306,730 | 10/1884 | Emery ................................. 73/859 X |
| 308,957 | 12/1884 | Emery ................................. 73/859 X |
| 3,224,259 | 12/1965 | De Nicola . |
| 3,368,834 | 2/1968 | Stratienko . |
| 3,501,183 | 3/1970 | Stratienko . |

OTHER PUBLICATIONS

Posit-Grip Products Division Brochure, Roller Bearing Company of America, West Trenton, N.J., Cat. 5007/77–5M.

*Primary Examiner*—Jerry W. Myracle

[57] ABSTRACT

A grip for a materials testing machine comprises a housing, first and second wedge members within the housing, the first wedge member having a gripping surface defining a test-specimen-receiving aperture and the second wedge member having an aperture for receiving the first wedge member, the wedge members being movable with respect to each other, and each of the wedge members having an inclined portion directed oppositely to the inclined portion of the other wedge member, and means for preloading the wedge members to cause them to move with respect to each other, whereby the wedge members interact to exert a gripping force on a test specimen through the first wedge member's gripping surface.

6 Claims, 1 Drawing Figure

U.S. Patent
Mar. 25, 1980
4,194,402
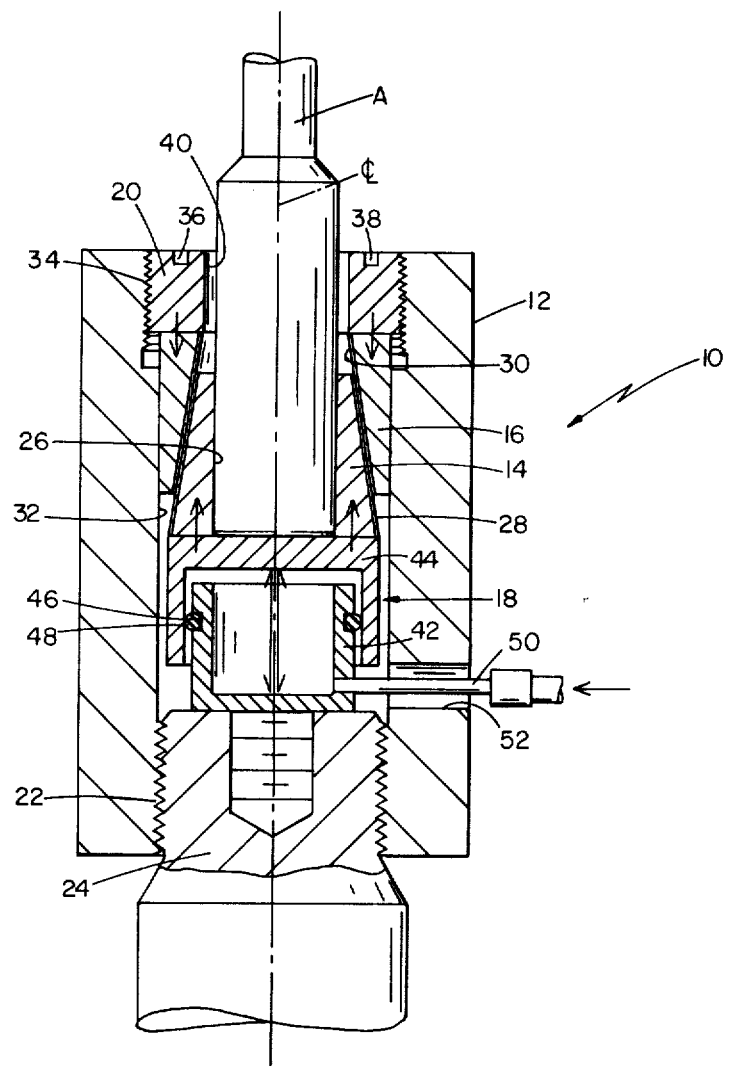

TESTING MACHINE GRIP

FIELD OF THE INVENTION

This invention relates to materials testing machines and in particular to test specimen grips for such machines.

BACKGROUND OF THE INVENTION

In dynamic testing a specimen of material is subjected to a variety of test loads. These include, e.g., tension, compression, and torsion, and some of these loads are under certain test conditions applied simultaneously to a specimen. The grips which secure a test specimen to permit the test machine to apply loads to the specimen are very important. A problem has been creation of unwanted, nonuniform stresses and strains in the specimen because of the way the grips are secured to it. For example, specimens have often been fabricated with threaded or button-shaped ends in order to be securely held by the grips. Machining of these specimen ends is time-consuming and difficult and introduces stress raisers in the specimen. Gripping of the preformed ends induces shear forces through the threaded or button ends of the specimen, leading to nonuniform stresses and strains and possible errors in the test results. It would be desirable to have a grip that does not require such preforming of the specimen ends, readily aligns the specimen, and grips it evenly and uniformly as well as strongly enough to permit the specimen to undergo severe testing.

My U.S. Pat. No. 3,224,259 describes a specimen grip in which a pair of externally wedge-shaped flat jaws ride against an internally oppositely wedge-shaped U-type flat frame whereby the force of the jaws' grip on a specimen is increased during operation as the jaws move relative to the frame and interact therewith through contacting wedging surfaces.

Stratienko U.S. Pat. No. 3,501,183 shows the use of a pair of axially interlocking wedges for securing a shaft to a surrounding member such as a gear or another shaft.

Stratienko U.S. Pat. No. 3,368,834 shows the use of a pair of radially and axially interlocking wedges for the same purpose as the first named Stratienko patent.

SUMMARY OF THE INVENTION

I have discovered a very strong grip for a materials testing machine that avoids the necessity of difficult machining of specimen ends and does not induce significant nonuniform stresses and strains in the specimen. My grip comprises a housing, first and second wedge members within the housing, the first wedge member having a gripping surface defining a test-specimen-receiving aperture and the second wedge member having an aperture for receiving the first wedge member, the wedge members being movable with respect to each other, and each of the wedge members having an inclined portion directed oppositely to the inclined portion of the other wedge member, and means for preloading the wedge members to cause them to move with respect to each other, whereby the wedge members interact to exert a gripping force on a test specimen through the first wedge member's gripping surface.

In preferred embodiments the first wedge member's aperture is cylindrical; the first wedge member has a frustoconical outer shape and is longitudinally split; the second wedge member's aperture is frustoconical in shape and is directed axially oppositely to the inclination of the first wedge member's outer shape; the second wedge member is longitudinally split, has a cylindrical outer shape, and is positioned in a cylindrical bore of the housing; the test specimen has two cylindrical ends for being received by first wedge members' apertures; the first and second wedge members have contacting surfaces that are made of low-friction material; the preloading means is a hydraulic power pack positioned axially adjacent to the end of the cylindrical bore; and there is a removable insert having a specimen-receiving aperture and retaining the wedge members within the housing's bore.

My invention provides a uniform, radial gripping force over a large area of a specimen end. The invention is simple, easy to make, inexpensive, and has few parts. Accurate, reliable materials testing is facilitated.

PREFERRED EMBODIMENT

I turn now to description of the structure and operation of a preferred embodiment of the invention, after first briefly describing the drawing.

DRAWING

The FIGURE is a side elevation view, partly in cross section, of the presently preferred embodiment of the invention.

DESCRIPTION

The FIGURE shows grip 10, which includes a housing 12, an inner annular wedge member 14, an outer annular wedge member 16, hydraulic power pack 18, and threaded retainer 20. Grip 10 is shown gripping test specimen A and is secured through cooperation of threaded female portion 22 of housing 12 with male threaded actuator rod 24 to the rest of a materials testing machine (not shown) such as manufactured by Instron Corporation of Canton, Mass. Such a machine has a power mechanism for applying loads to a specimen through actuator rod 24 and a pair of grips 10 (only one is shown in the FIGURE, as the other is identical to it), a control mechanism for regulating and varying the load, and a readout mechanism for showing the results of the testing.

The bottom of inner wedge member 14 rests on the top of power pack 18, which in turn rests on top of actuator rod 24. Inner wedge member 14 is frustoconically shaped on its exterior, has a cylindrical bore 26 extending therethrough, and is longitudinally split (not shown) to facilitate radial compression and expansion. Test specimen A has a cylindrically machined end that fits within bore 26 and rests on power pack 18. The inclined outer walls of wedge member 14 are coated with a low-friction substance 28 such as Teflon (DuPont trademark for polytetrafluoroethylene). Similarly the inner inclined walls of wedge member 16 are coated with low-friction substance 30. Wedge member 16 is also longitudinally split (not shown).

Further characteristics of wedge members 14 and 16 and other wedge members suitable for use in the invention are described in a 1977 brochure published by the Posit-Grip Products Division of Roller Bearing Company of America, Sullivan Way, West Trenton, N.J. 08628, entitled "Posit Grip Products", and the contents of that brochure are hereby incorporated by reference herein.

The interior of outer wedge member 16 is frustoconical in shape, while its outer surface is cylindrical and fits within cylindrical bore 32 of housing 12. Housing 12 terminates at its upper end in female threaded portion 34, which receives retainer 20. Retainer 20 has grooves 36, 38 for receiving a spanner wrench for insertion or removal of the retainer. Outer wedge member 16 abuts retainer 20, and specimen A extends through bore 40 in retainer 20. As shown, wedge member 14 decreases in thickness in an upward (of course "upward" could also be "sideward" or "downward", depending on the specimen's and machine's orientation) direction, whereas outer wedge member 16 increases in thickness in an upward direction. Wedge members 14, 16 are axially movable with respect to each other, both have a 3°20' taper on their inclined surfaces, and low-friction surfaces 28 and 30 each have a coefficient of friction of 0.05. Both wedge members are retained within housing 12 by retainer 20.

Hydraulic power pack 18 includes container 42 and axially movable cover 44 in the shape of an inverted cup. Annular groove 46 in container 42 holds O-ring 48 to prevent fluid from leaking out of container 42. Fluid line 50 extends into container 42 through a hole in the wall and a larger hole 52 in the wall of housing 12. Line 50 extends away from housing 12 to a hydraulic pump (not shown).

Operation

In operation, a cylindrical end of specimen A is inserted into grip 10. The cylindrical end slides down through inner wedge member bore 26 until it contacts cover 44 of power pack 18. Then fluid from the hydraulic pump passes through line 50 into power pack container 42 to expand the power pack. Cover 44 is biased upwardly under the hydraulic pressure against the end of the specimen and inner wedge member 14, while container 42 is biased downwardly with an equal and opposite force against actuator rod 24. The bias of power pack 18 thus preloads the actuator rod thread, causes the wedge member 14 to wedge into wedge member 16, thereby to clamp specimen A tightly along bore 26, and prestresses the retainer thread. Longitudinal splitting of member 16 facilitates its radial expansion within bore 32 to press tightly against housing 12. The load applied by power pack 18 should be approximately 10% higher than the tensile or compressive load that the specimen will see under test conditions. With all the elements thus prestressed, the grip will be a linear spring, and uniform loading will be applied to the test specimen. Normally, there will be during clamping some axial, upward movement of inner wedge 14 under the bias of cover 44, and the testing machine is put in a mode that allows such movement. The specimen can now be tested.

Power pack 18 permits rapid clamping and removal of a test specimen.

When specimen A is to be removed, the hydraulic pressure on power pack 22 is relieved, retainer 20 is removed with a spanner wrench, and then the specimen and wedge members are removed. The low-friction coatings 28 and 30 and the angle of taper are such that the wedge members are self-releasing.

Grip 10 (in combination with an identical grip at the other end of the specimen) automatically aligns the specimen with actuator rod 24 along the centerline shown.

Modifications and Variations

One could preload the wedge members by other means than a hydraulic power pack. For example, instead of retainer 20, a cap could be axially bolted onto the end of housing 12. One could use more than two wedge members. Likewise one could use wedge members that have inclined portions that extend peripherally instead of axially or a combination of both types of inclination, all as described in Stratienko U.S. Pat. No. 3,368,834.

Other embodiments within the invention will occur to those skilled in the art.

Incorporation by Reference

I hereby incorporate by reference the contents of Stratienko U.S. Pat. No. 3,368,834 and Stratienko U.S. Pat. No. 3,501,183.

What is claimed is:

1. In a materials testing machine of the type having
   a pair of grips for gripping two ends of a test specimen,
   power means for applying loads to said test specimen through said grips, and
   control means for controlling said power means,
   the improvement wherein each of said grips comprises:
   a housing,
   at least first and second wedge members positioned in said housing,
      each of said wedge members having an aperture therethrough, the aperture of said first wedge member positioned for receiving a test specimen and said first wedge member having a gripping surface defining its said aperture, and the aperture of said second wedge member positioned for receiving said first wedge member, said wedge members being movable with respect to each other and each of said wedge members having an inclined portion directed oppositely to the inclined portion of said other wedge member, and
   means for preloading said wedge members to cause them to move with respect to each other,
   wherein said wedge members are annular,
   wherein said apertures are circular in cross section,
   wherein said aperture of said first wedge member and said gripping surface are cylindrical, said first wedge member has a frustoconical outer shape, said aperture of said second wedge member is frustoconical in shape and is directed axially oppositely to said inclination of said first wedge member's outer shape, said second wedge member has a cylindrical outer shape, said housing has a cylindrical bore for receiving said second wedge member,
   wherein said first wedge member is longitudinally split,
   whereby said wedge members interact to exert a gripping force on said test specimen through said first wedge member's gripping surface.

2. The machine of claim 1 said first and second wedge members have contacting surfaces that are made of low-friction material.

3. The machine of claim 2 wherein said means for preloading is a hydraulic power pack.

4. The machine of claim 3 wherein said power pack is disposed axially adjacent to the end of said cylindrical bore.

5. The machine of claim 1 wherein said grip further includes a removable insert having an aperture and retaining said wedge members within said bore, said aperture receiving said test specimen.

6. The machine of claim 1 wherein said second wedge member is longitudinally split.

* * * * *